(12) United States Patent
Evans

(10) Patent No.: US 8,092,366 B2
(45) Date of Patent: Jan. 10, 2012

(54) SLING ANCHOR SYSTEM

(75) Inventor: Doug Evans, Snellville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 734 days.

(21) Appl. No.: 12/093,493

(22) PCT Filed: Nov. 14, 2006

(86) PCT No.: PCT/US2006/044315
§ 371 (c)(1),
(2), (4) Date: Jul. 14, 2008

(87) PCT Pub. No.: WO2007/059199
PCT Pub. Date: May 24, 2007

(65) Prior Publication Data
US 2009/0221868 A1    Sep. 3, 2009

Related U.S. Application Data

(60) Provisional application No. 60/736,219, filed on Nov. 14, 2005, provisional application No. 60/749,774, filed on Dec. 13, 2005, provisional application No. 60/754,540, filed on Dec. 28, 2005.

(51) Int. Cl.
*A61F 2/02* (2006.01)
(52) U.S. Cl. .......................................................... 600/30
(58) Field of Classification Search .............. 600/29–32, 600/37; 128/885; 606/151
See application file for complete search history.

(56) References Cited

U.S. PATENT DOCUMENTS

| | | | |
|---|---|---|---|
| 7,131,943 B2 * | 11/2006 | Kammerer | 600/30 |
| 2006/0089525 A1 * | 4/2006 | Mamo et al. | 600/37 |
| 2007/0078295 A1 * | 4/2007 | Landgrebe | 600/37 |

* cited by examiner

*Primary Examiner* — Charles A Marmor, II
*Assistant Examiner* — Christine Hopkins
(74) *Attorney, Agent, or Firm* — Rutan & Tucker, LLP

(57) ABSTRACT

The present disclosure is generally directed to surgical articles useful for implanting support members in patients. The articles disclosed herein include a support member, such as a sling for urinary incontinence, tissue anchors, filamentary elements for associating the support member with the anchors, and introducer needles for placing the anchors in a patient. The support members can also be configured for use in pelvic floor repair, such as for treating cystoceles, rectoceles, and enteroceles.

6 Claims, 21 Drawing Sheets

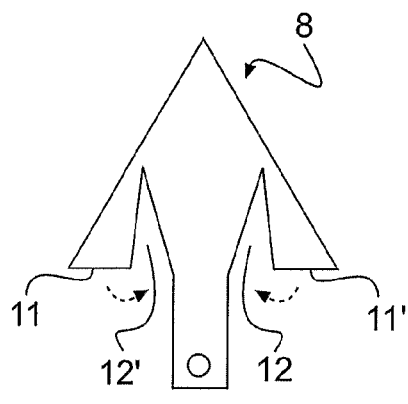
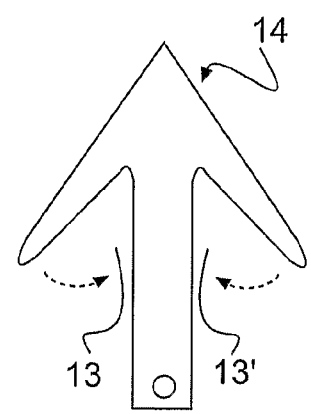
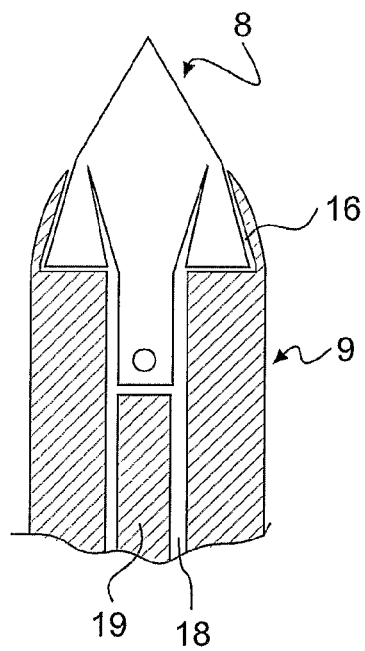
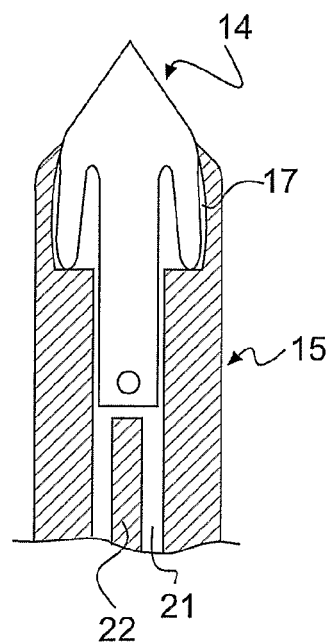
FIG. 1E  FIG. 1F

SLING ANCHOR SYSTEM

This application is a U.S. national stage application under 35 U.S.C. §371 of International Application No. PCT/US2006/044315, filed Nov. 14, 2006, claiming priority to U.S. Provisional Application Nos. 60/736,219, filed Nov. 14, 2005; 60/749,774, filed Dec. 13, 2005; and 60/754,540, filed Dec. 28, 2005, the disclosures of which are all incorporated herein by reference in their entirety.

The present invention relates generally to the treatment of stress urinary incontinence using at least one of an improved anchor, introducer system, and tensioning system.

An increasingly widespread technique for treating urinary incontinence is that of sling suspension. Examples of such procedures and equipment that can be employed are discussed in U.S. Pat. Nos. 5,112,344, 5,899,909, and 6,273,852; and U.S. Patent Application Publication Nos. U.S. 2004/0144395, and U.S. 2006/0015069, the disclosures of which are all incorporated by reference herein in their entirety.

Generally, sling suspension procedures involve the placement of a sling member beneath the patient's urethra. The sling member is suitably implanted in the patient's tissue by using an introducer needle to help draw the tissue implant sling into position.

Slings have been made from tape or mesh. Numerous implant materials have been considered and used for sling procedures, including both synthetic and natural materials.

A traditional sling procedure involves placing a strip of an implant material (natural tissue or synthetic mesh) under the urethra and securing it to the rectus fascia or other portions of the patient's anatomy with sutures to hold the implant in position during the healing process.

Techniques have been developed that speed the implant process, by reducing the number of incisions made and altering the pathways by which the tissue implant is introduced into the body. These improvements, which employ specialized instrumentation, help to reduce operative time and have made the procedure less invasive.

These techniques generally require that an implant be joined to an introducer needle. Typically, the implant is inserted into, and pulled through the body. Then, in a subsequent step, the implant is detached from the introducer needle. A deficiency with existing introducer devices, however, is that they are typically unwieldy, awkward, and it can be time consuming to attach and/or detach an implant to or from an introducer device.

Accordingly, it could be advantageous to provide a system for implanting an article that avoids at least one of the foregoing deficiencies.

According to various embodiments, the present disclosure is directed to an implantable system comprising at least two tissue anchors, at least two filamentary elements adapted to be associated with the at least two tissue anchors, and a support member comprising at least two connectors, wherein the at least two connectors are adapted to associate the support member with the at least two filamentary elements, and wherein at least one of the at least two connectors is adapted to adjustably and releasably fix a filamentary element.

According to various embodiments, the present disclosure is directed to a method for providing support for a female urethra, comprising creating an incision in the anterior vaginal wall just below the urethral meatus, advancing an introducer needle through the incision and towards the direction of one of the two obturator foramen where the introducer needle has a tissue anchor connected to its distal end, and releasing the anchor from the introducer needle, wherein the anchor is connected to a support member via a filamentary element.

According to various embodiments, there is provided a kit for providing support to a female urethra, comprising at least one introducer needle, at least two soft tissue anchors adapted to be connected to the at least one introducer needle, and at least one implantable article comprising a support portion, wherein the implantable article comprises at least two connectors, each of which has at least one filamentary element attached thereto, and wherein the at least two connectors each contain at least one perforation for adjustably and releasably fixing a filamentary element.

BRIEF DESCRIPTION OF THE DRAWINGS

The present invention is further described in the detailed description which follows, in reference to the noted drawings, by way of non-limiting examples of certain embodiments of the present invention, in which like characters represent like elements throughout the views of the drawings, and wherein:

FIG. 1E illustrates a configuration of an anchor seated in the distal end of an introducer needle in accordance with various aspects of the present disclosure.

FIG. 1F illustrates a configuration of an anchor seated in the distal end of an introducer needle, in accordance with various aspects of the present disclosure.

FIGS. 6A-F illustrate various introducer needles in accordance with various aspects of the present disclosure.

FIGS. 6A-B illustrates an introducer needle in accordance with various aspects of the present disclosure.

The present disclosure is directed generally to various systems, methods, and articles of manufacture suitable for treating various disorders including, by way of example, at least one of urinary incontinence, rectocele, cystocele, and enterocele. However, the systems, methods, and article of manufacture disclosed herein can also have other uses. For example, they may be used to provide adjustable tension between two points, such as ligaments, tendons, etc., within the body. The systems disclosed herein provide advantages over prior art systems. For example, the anchors disclosed herein can be used as the tissue dissectors. Also, according to various embodiments, the anchors can provide both one- and two-way adjustability.

Figure 1A:
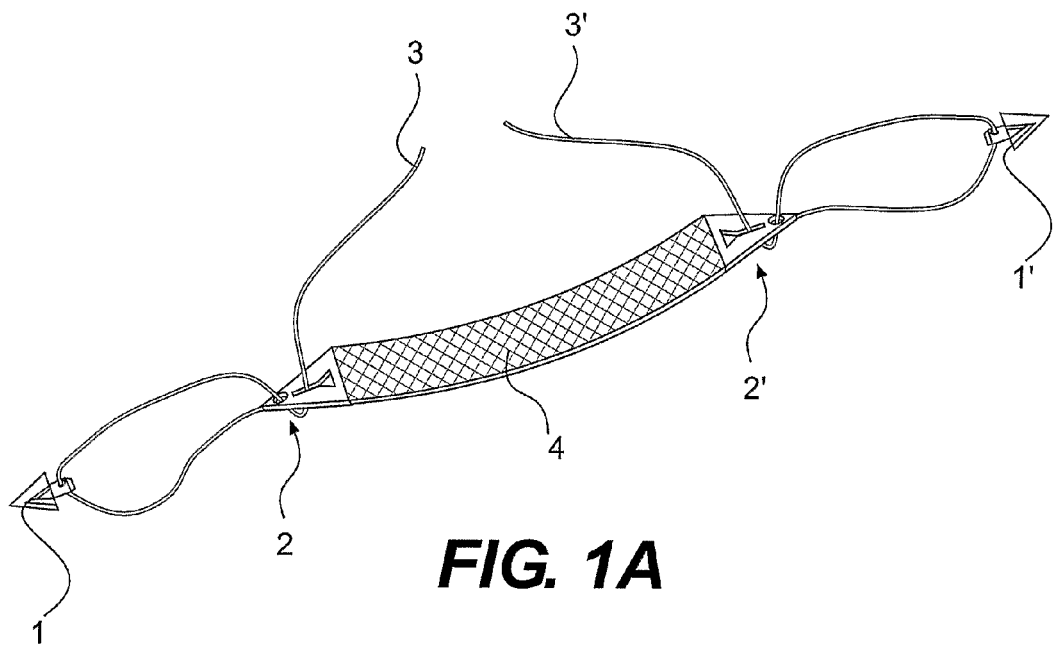
FIG. 1A illustrates one embodiment of an implantable system in accordance with the present invention.

FIG. 1A illustrates one embodiment of an implantable system according to various embodiments. Tissue anchors 1 and 1' are adapted to be inserted and anchored into body tissue, such as ligament, muscle, fascia, and other tissues capable of holding an anchor. Support member 4 is configured to provide support to tissue within the body, such as a urethra, bladder neck, bladder, rectum, etc. The support member 4 comprises connectors 2 and 2'. The connectors 2 and 2' are, according to various embodiments, attached to support member 4. The connectors may be a separate article from the support member, and is joined during the manufacturing process by methods well-known to the ordinary practitioner, such as heat bonding, adhesive application, etc. According to another embodiment, the connectors are integral with the support member 4. According to another embodiment, the connectors are designed to be joined to support member 4 in a securable fashion by a physician.

Figure 1B:
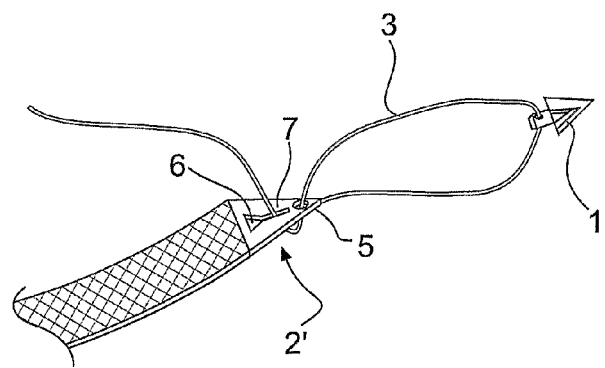
FIG. 1B is an expanded view of one embodiment of the implantable system according to FIG. 1A.

With reference to FIGS. 1A and 1B, filamentary elements 3 and 3' associate 1 the support member with the anchors 1 and 1', respectively. According to various embodiments, and with reference to the right side of the implantable system, one end of the filamentary element 3' is permanently attached to connector 2', which in turn is connected to support member 4. The other end of filamentary element 3' is first threaded through tissue anchor 1', and is then threaded through a first aperture 5 in connector 2', and then through a second aperture 6 in the connector. According to various embodiments, second aperture 6 contains a cleating member 7, so that the free end of the filamentary element 3 can be releasably fixed in connector 2'. According to various embodiments, filamentary element 3' and aperture 5 in connector 2' allows the physician to adjust the tension of the support member 4 when, e.g., it is looped beneath a urethra.

By way of illustration, and with reference to FIG. 1A, anchor 1 may be secured in the obturator internus muscle, the support member may be disposed underneath the urethra, and then anchor 2' may be disposed in the contralateral obturator internus muscle. It can then be desirable to adjust the tension exerted by the support member on the urethra by pulling on at least one of the two filamentary elements 3 and 3'. When the desired amount of tension is obtained, the physician may then secure one or both filamentary elements by passing them through both apertures in the connector and laterally into the cleating member.

Figure 1C:
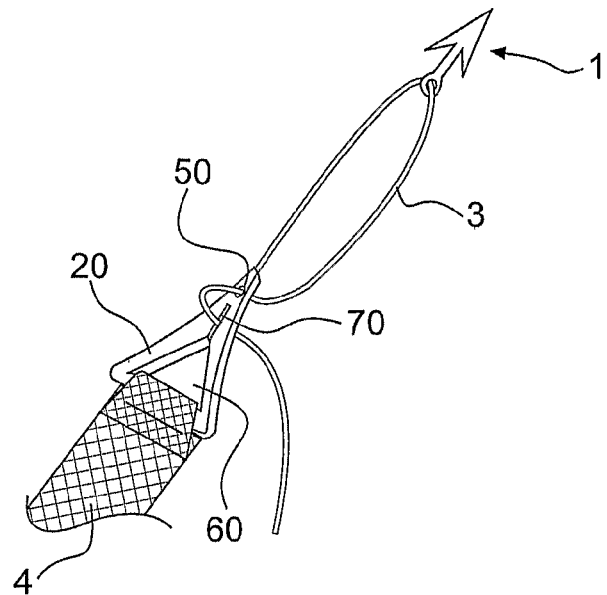
FIG. 1C illustrates an expanded view of one component of an implantable system in accordance with the present disclosure.

FIG. 1C illustrates another embodiment of a portion of an implantable system according to various embodiments. One end of filamentary element 3 is permanently secured in connector 20, and a free end of the filamentary element is drawn through an aperture in tissue anchor 1, through aperture 50, through aperture 60, and then secured in cleating member 70. Aperture 60 differs from aperture 6 in FIGS. 1A-1B in that aperture 60 is larger. The connector 20 comprises less material, which serves to minimize tissue trauma and abrasion, thereby reducing the risk of erosion to surrounding tissue. According to various embodiments, the edge comprising the internal circumference of aperture 60 can be blunted and rounded, such that no sharp edges are presented that might damage surrounding tissue.

Figure 1D:
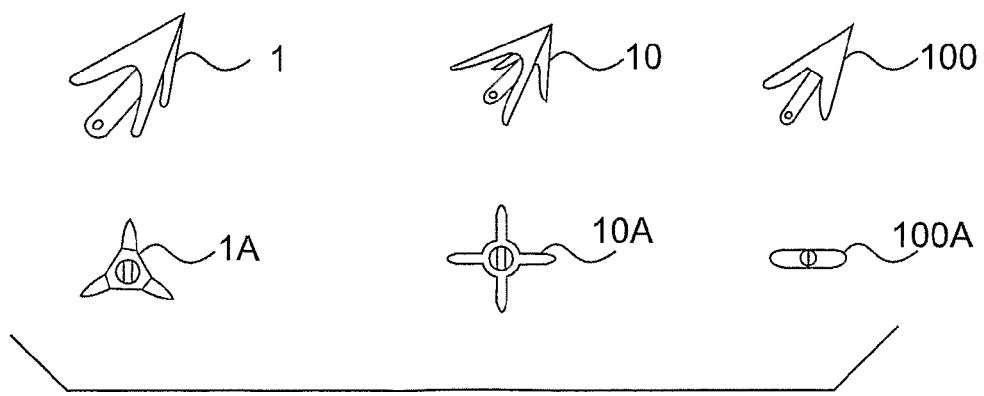
FIG. 1D illustrates various anchors from side and bottom perspectives, in accordance with the present disclosure.

According to various embodiments, FIG. 1D illustrates exemplary anchors useful in accordance with the present disclosure. Anchor 1 is a three barbed anchor, having a view 1A from the bottom of the anchor; anchor 10 is a four-barbed anchor, having a view from the bottom 10A; and anchor 100 is a two barbed anchor, with a view from the bottom 100A. Those of ordinary skill in the art will appreciate that various types of anchors may be used in accordance with the present disclosure, depending on the anchoring properties sought.

FIG. 1E illustrates the configuration of a tissue anchor 8 in the distal end of an introducer needle 9. The tissue anchor 8 has barbs 11 and 11' that extend laterally from its longitudinal axis. The barbs 11 and 11' are flexible in a direction substantially perpendicular to the longitudinal axis of the anchor, such that they can be urged toward or away from the longitudinal axis. This flexibility allows the anchor 8 to be securely seated in the distal end of the introducer needle 9 until the anchor is purposefully discharged into tissue by the physician.

As illustrated in FIG. 1E, the cavities 12 and 12' formed by the space between the anchor body and the barbs angles slightly away from the anchor body as the cavities extends towards the distal end of the anchor 8. This angle, combined with the wider proximal ends of the barbs, permits the anchor to be seated in the introducer needle with minimal flexing.

FIG. 1F illustrates another exemplary configuration of an anchor 14. There, the cavities 13 and 13' formed between the anchor body and the barbs extends distally in a direction parallel to the longitudinal axis of the anchor body. The proximal ends of the anchor barbs are also narrow relative to the proximal ends of the anchor barbs of anchor 8. This configuration may be desirable when anchors with a wider profile are desirable, such as for greater anchoring ability in a softer tissue.

The distal end of the introducer needles 9 and 15 have cavities 16 and 17, respectively, dimensioned to receive and securely house at least a portion of the anchors. An internal lumen 18 of introducer needle 9 comprises a stylet member 19, which is actuated in a distal direction by a control mechanism, such as a button-actuated spring (not shown). Similarly, internal lumen 21 of introducer needle 15 comprises a stylet member 22. Suitable actuating mechanisms are well-known in the art, and the selection of one over the other is a matter well-within the skill of the ordinary practitioner.

Figure 1G:
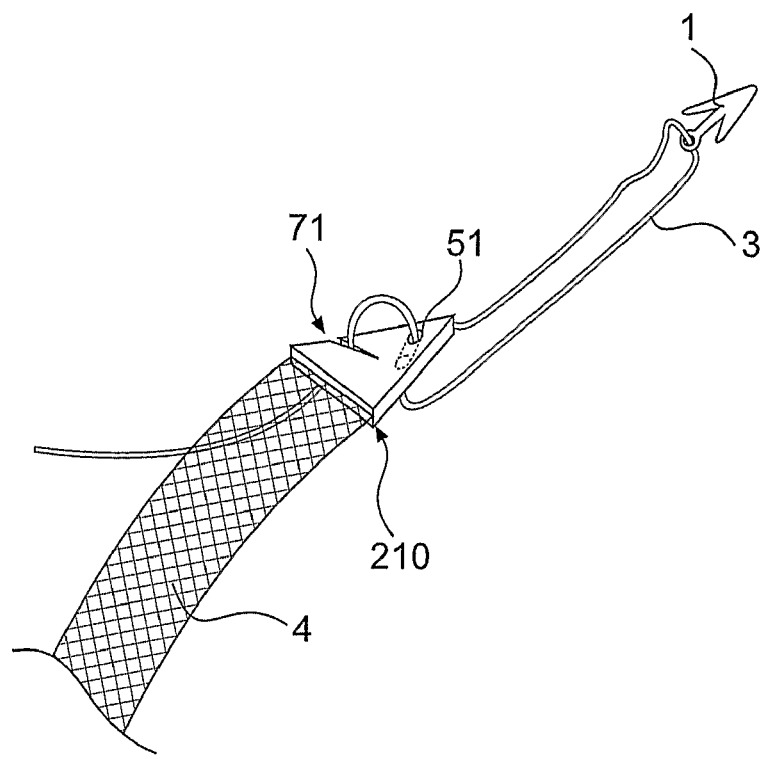
FIG. 1G illustrates an aspect of an implantable system in accordance with various aspects of the present disclosure.

According to various embodiments, FIG. 1G illustrates another suitable implantable system in accordance with the present disclosure. This implantable system comprises an anchor 210 with an aperture 51 and a cleating member 71. Cleating member 71 extends radially from the center, or near the center, of the connector and towards a lateral edge of the connector, much like a cleating member in a spool of thread. Filamentary element 3 extends from a permanent connection at the tip of connector 210, through an aperture in anchor 1, through aperture 51, and then into cleating member 71.

Figure 1H:
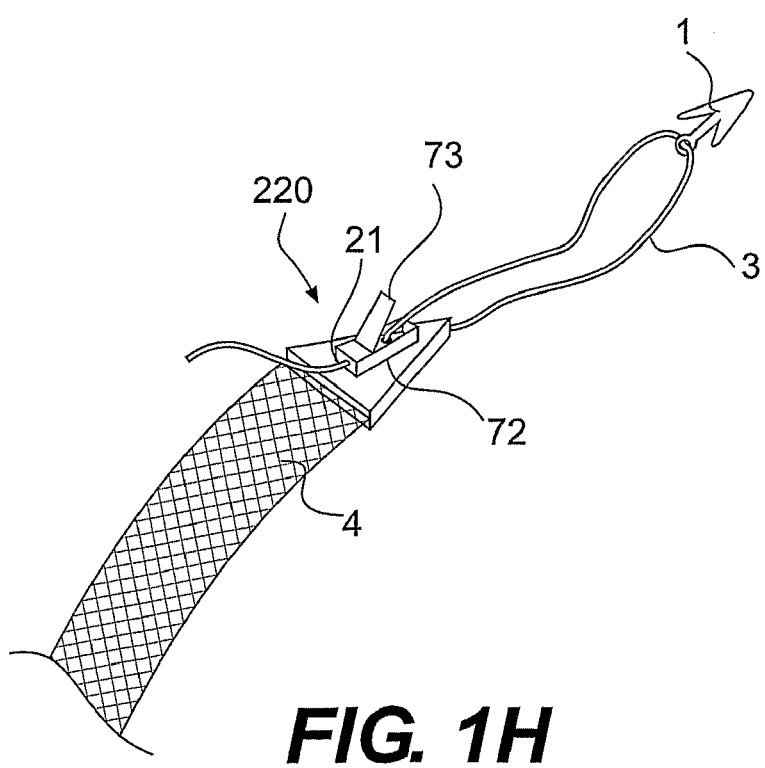
FIG. 1H illustrates an aspect of an implantable system in accordance with various aspects of the present disclosure.

FIG. 1H illustrates another connector in accordance with various embodiments. Connector 220 comprises a locking housing 72, with an internal lumen and a locking member 73. The filamentary element 3 is permanently connected at one end to connector 220, drawn though an aperture in anchor 1, and then though the locking housing 72. When the desired amount of filamentary element is drawn through locking housing 72, the locking member 73 is depressed into engagement with the housing to secure the filamentary element.

Figure 1I:
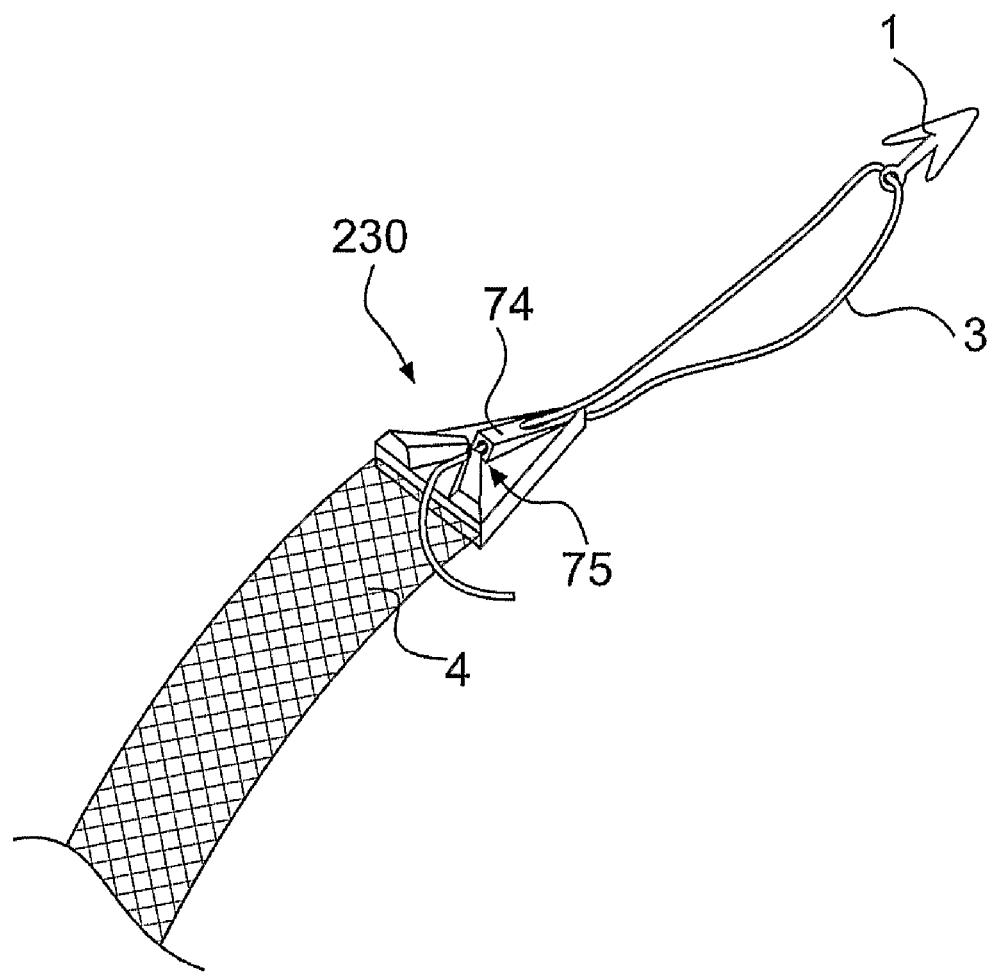
FIG. 1I illustrates an aspect of an implantable system in accordance with various aspects of the present disclosure.

Another exemplary connector 230 is illustrated in FIG. 1I. There, an external cleating element 75 is disposed proximate to lumened member 74. The filamentary element extends from a permanent connection at connector 230, through an aperture in anchor 1, and through lumened member 74 and towards external cleating element 75, wherein it may be fixed as shown.

Figure 2:
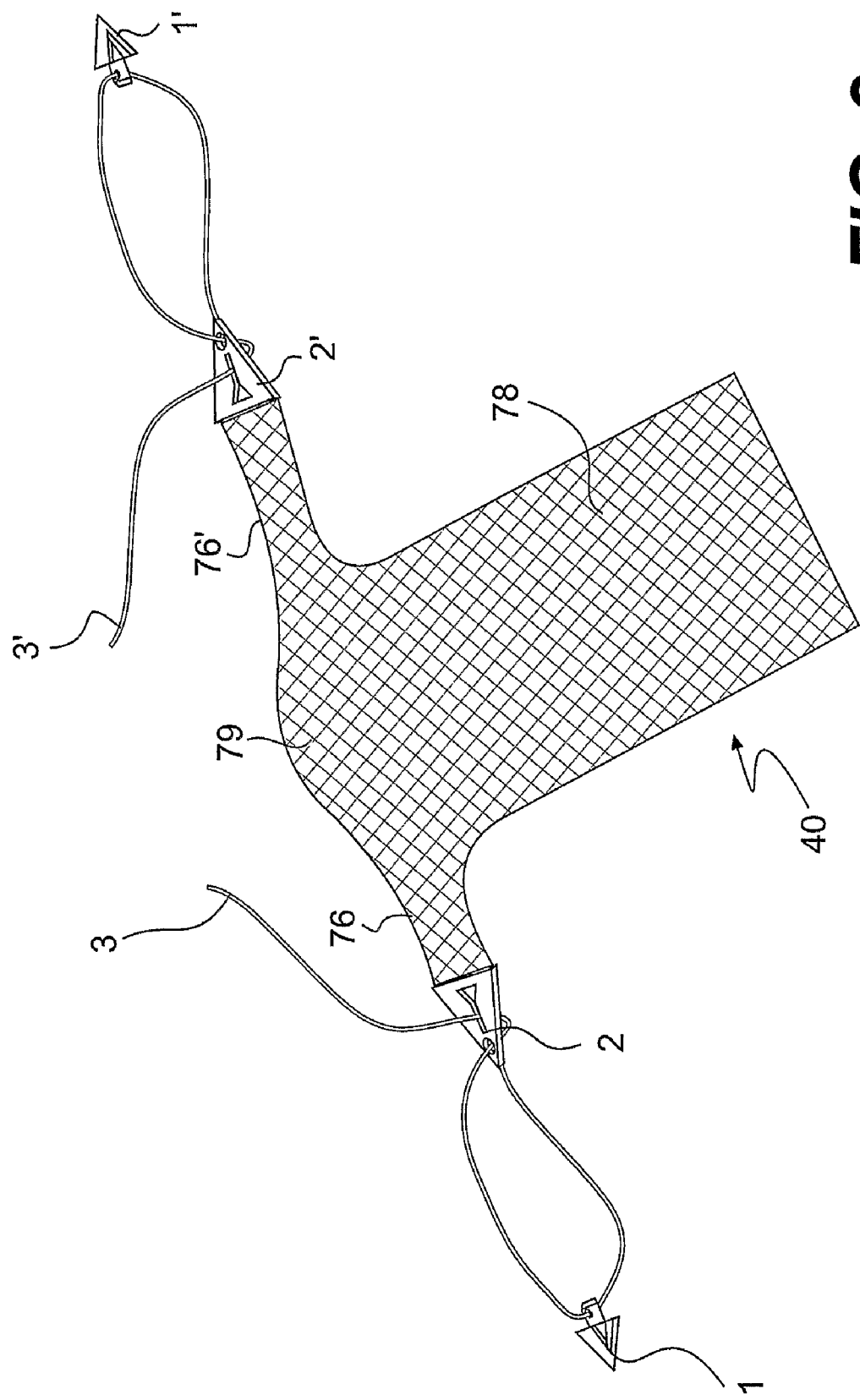
FIG. 2 illustrates an implantable system having a large central support body in accordance with various aspects of the present disclosure.

FIG. 2 illustrates one embodiment of an implantable system having a broad central support area in support member 40. Support member 40 is characterized by two lateral ends 76 and 76' terminating in connectors 2 and 2'; a central support body 78 extending in one direction; and a support portion 79 extending in the opposite direction.

Figure 3:
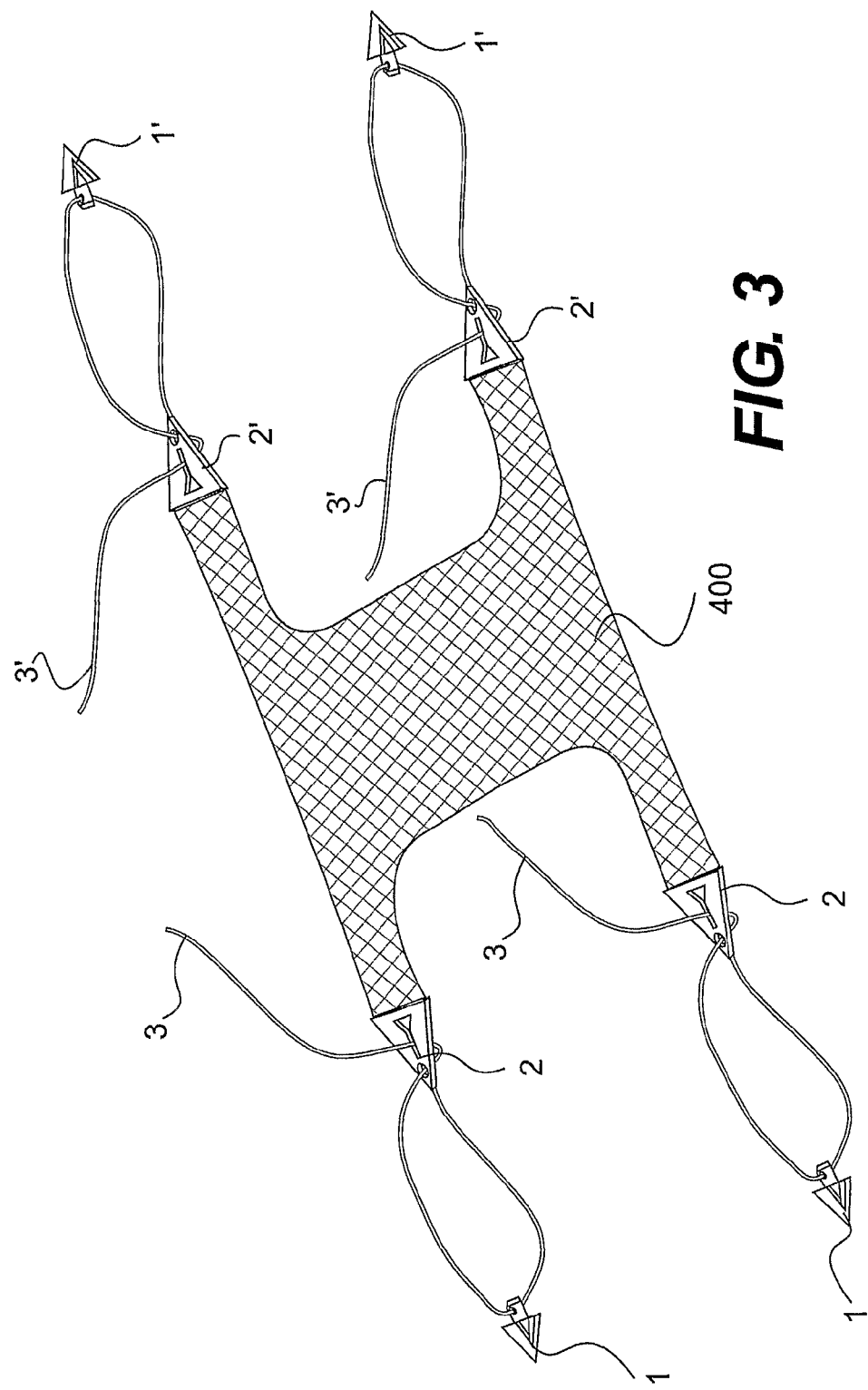
FIG. 3 illustrates an implantable system configured for prolapse repair, in accordance with various aspects of the present disclosure.

According to various embodiments, FIG. 3 illustrates another embodiment of an implantable system. This embodiment comprises a support member 400 configured for vaginal prolapse repair, and is characterized by four arms, each of which terminates in respective connectors. The support member may be configured to treat various pelvic floor disorders such as, for example, a cystocele, which is a condition whereby the bladder descends into the vaginal vault.

The support member can be made of any suitable biocompatible material. For example, the support member can be made of a permanent material, partially bioabsorbable material, completely bioabsorbable material, or any combinations thereof. In some embodiments, the synthetic material comprises knitted monofilament, polypropylene mesh having multidirectional elasticity that provides long-term reinforcement of pelvic support structures. Irrespective of the material used to construct the implants, according to various embodiments the implants are highly flexible yet have the strength needed for tissue support.

The material can be a synthetic mesh, such as polypropylene mesh or bioabsorbable PLA. The support member can comprise a biological material, such as porcine dermal tissue, cadaveric tissue, collagen-based mesh, or other biological material suitable for implantation into an animal (e.g., human) body. The support member can comprise an identification element, such as one or more colored threads, or differently-shaped arms, to enable the physician to identify and track various aspects of the support member during placement.

According to various embodiments, suitable non-limiting examples of materials that can serve as support members include acellular porcine dermal tissue. Such dermal material is typically processed to render it biocompatible. One scheme for preparing biocompatible porcine dermal tissue is set forth in U.S. Pat. No. 5,397,353 to Oliver et al, and owned by Tissue Science Laboratories PLC, of Aldershot, Hampshire, U.K. Such material is commercially available as Pelvicol™ implant material, distributed by C. R. Bard, Inc. of Murray Hill, N.J., and produced by Tissue Science Laboratories PLC. Another suitable material is CollaMend™ implant, which is a sterile, off-white sheet of lyophilized acelluural porcine dermal collagen that retains its constituent elastin fibers. CollaMend™ implant is also available from C. R. Bard, Inc.

The support member can have any dimensions suitable for its intended purpose. The support member can be narrow or wide, depending on the organ and/or tissue to be supported. For example, when used to support the urethra, the support member can have a width ranging from about 5 mm to about 20 mm, for example about 8 to about 12 mm. The length can range from about 2 to about 15 cm, for example from about 3 to about 10 cm.

The tissue anchor can be made of any suitable biocompatible material. By way of non-limiting example, suitable tissue anchors in accordance with the present disclosure can be constructed of silicone, stainless steel, Dacron, polypropylene, and any combination of the foregoing. The tissue anchors can be permanent, partially bioabsorbable, or completely bioabsorbable. Suitable non-limiting examples of bioabsorbable material include PLA copolymers, such as poly (L/D lactide) acid having a high inherent viscosity.

According to various embodiments, the tissue anchor provides fixation of the implantable systems disclosed herein. The anchors are designed to anchor into soft tissue such as muscle, fascia, and ligaments. The anchors have barbs that lock into the surrounding tissue when pressed into position. The barbs may be compressed initially during insertion, then expanded outwards when lodged into surrounding tissue, or they may be in an expanded position before, during, and after placement. According to various embodiments, the anchors are configured to hold a portion of a filamentary element. This configuration can comprise an aperture, or eyelet, disposed at the proximal end of the anchor that permits passage (and, optionally, fixation of) the filamentary element.

The anchor can optionally include a locking mechanism. For example, the locking mechanism can permit preferential, or one-way, movement of the filamentary element. This may be accomplished by a variety of means, such as by providing an eyelet bordered by a series of angle barbs. Suitable non-limiting examples of such anchors may be found in U.S. Patent Application Publication No. U.S. 2005/0256530, the disclosure of which is incorporated herein by reference in its entirety.

The filamentary element is designed to associate the support member with a tissue anchor. According to various embodiments, the filamentary element can be comprised of a variety of materials. It can comprise a permanent or bioabsorbable material. The filamentary element can comprise the same materials as, and optionally be integral with, the support member. According to various embodiments, the filamentary element can be a single- or multi-strand filament, such as single- or multi-strand polypropylene.

According to various aspects of the present disclosure, the implantable support system disclosed herein comprises at least one introducer needle. The introducer system disclosed herein provides a simple and efficient way to implant a support member, such as a urethral sling or a prolapse repair implant. The introducer needle may comprise a hook-shaped introducer needle that can be used for placing both arms of an implant, or it can comprise a helical or halo-shaped needle. According to various embodiments, a kit comprising a helical or halo-shaped needle would comprise two needles, a left version and a right version, for placing each end of the implantable system in a patient.

The introducer needles disclosed herein can be made of any suitable biocompatible material such as stainless steel, nitinol, etc. If desired, the introducer needle could be coated with a low-friction layer of material (not shown) such as PTFE to reduce insertion trauma. According to various embodiments, the introducer needle and/or the support member can comprise an external sleeve. Such a sleeve could serve two purposes. First, if made of PTFE or similar material, it could provide a lubricious surface to ease passage of the introducer needle and/or the support member through the body, while at the same time minimizing injury to tissue. Secondly, the sleeve could be made of a bright color, such as green or blue, to improve visibility during an optional cytoscopy to confirm bladder integrity. Even if bladder perforation is not observed, the bright color of the sleeve can be seen through the thin bladder wall, confirming same placement of the introducer needle.

Figure 4A:
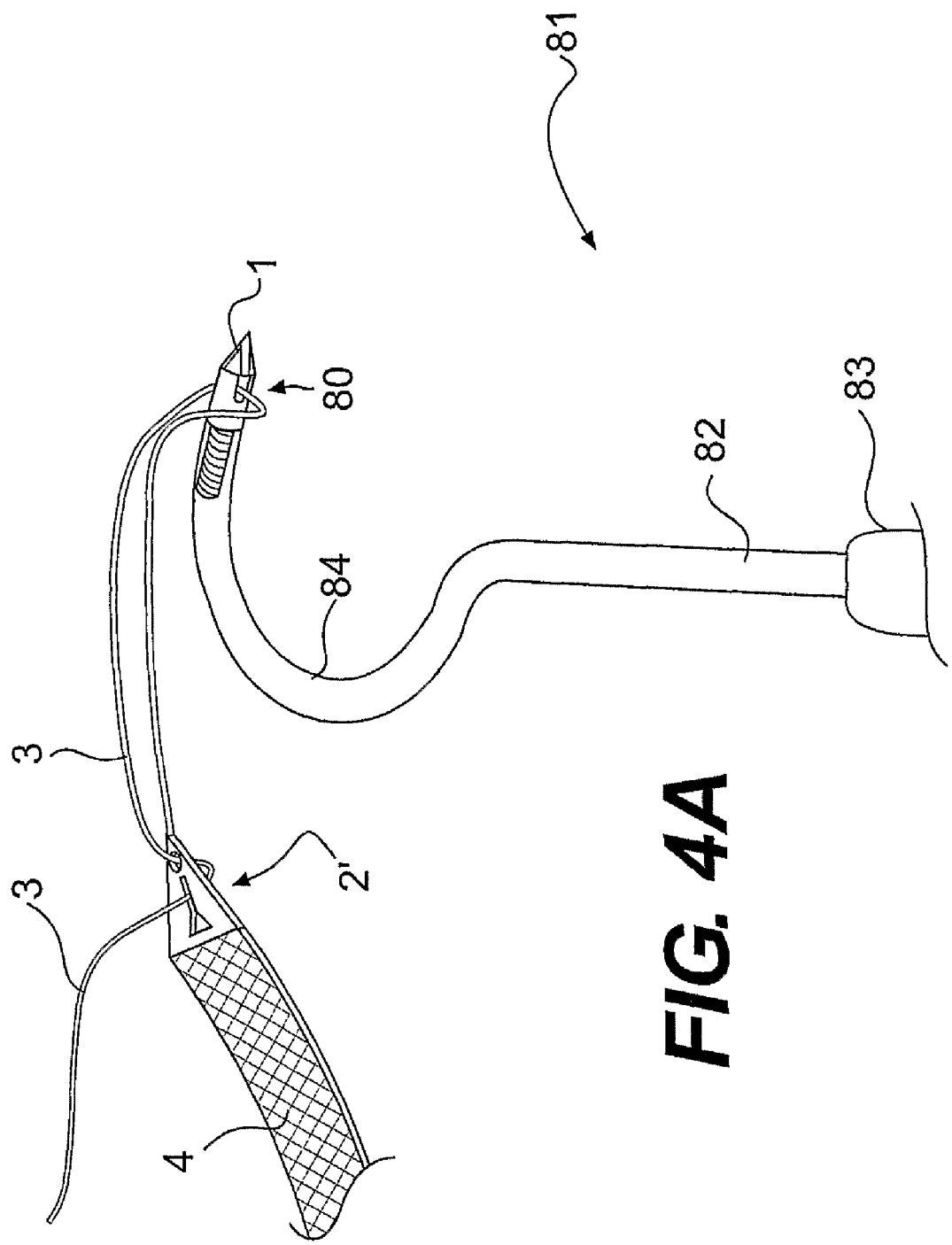
FIG. 4A illustrates an example of a curved introducer needle associated with an implantable system in accordance with various aspects of the present disclosure.
Figure 4B:
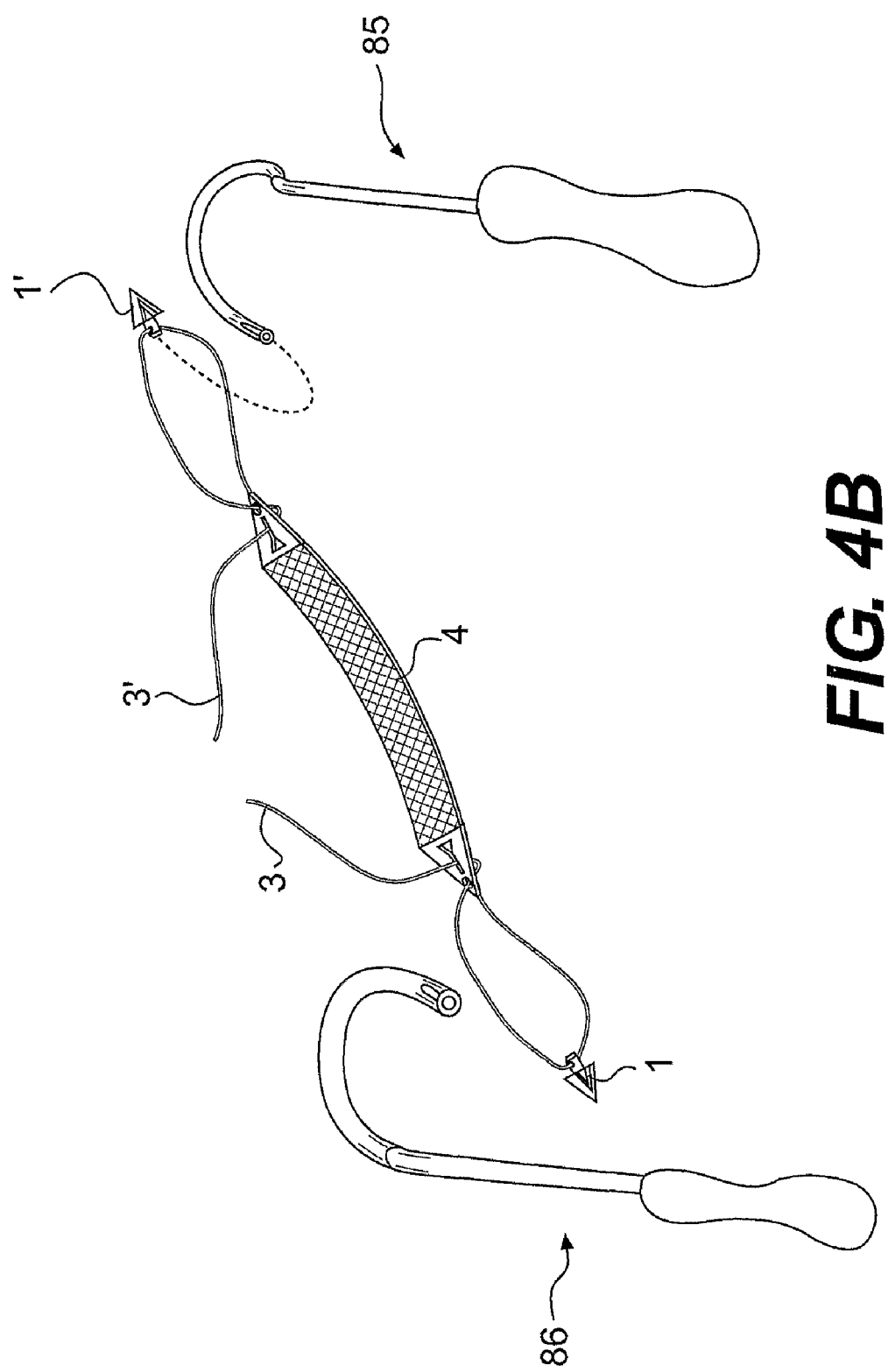
FIG. 4B illustrates various components of a kit for supporting the urethra, in accordance with various aspects of the present disclosure.
Figure 4C:
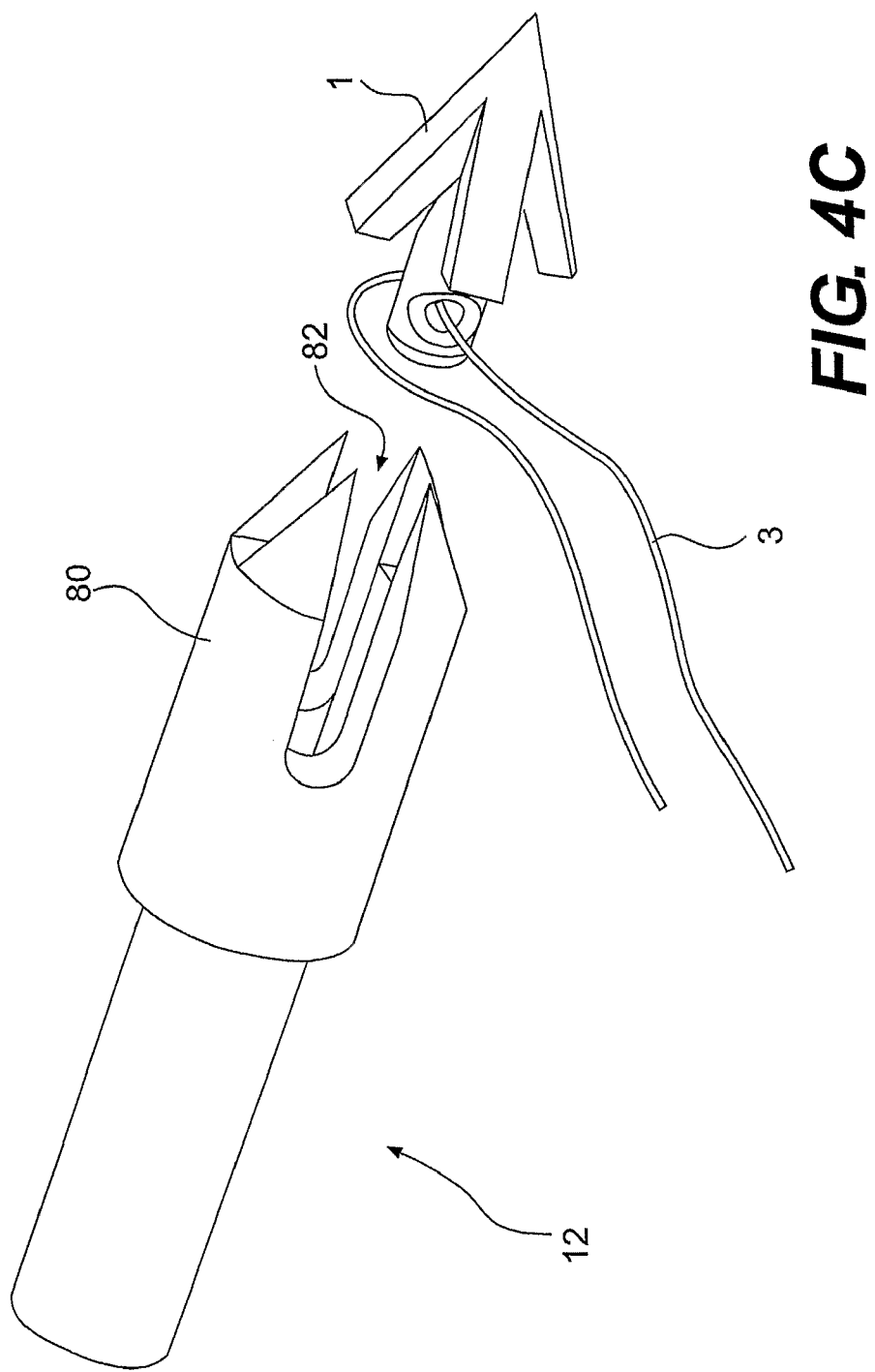
FIG. 4C illustrates an expanded view of an anchor and the distal end of an introducer needle, in accordance with various aspects of the present disclosure.

FIGS. 4A-4C illustrates an embodiment whereby tissue anchor 1 is mounted on the distal end 80 of introducer needle 81. Referring to FIG. 4A, introducer needle 81 comprises a shaft having a straight proximal portion 82 terminating in handle 83, and curved distal portion 84. The filamentary element 3 is looped through anchor 1, and the entire assembly is ready for use. According to various embodiments, FIG. 4B illustrates various aspects of a kit for treating urinary incontinence, including two halo needles 85 and 86, support member 4, filamentary elements 3 and 3', and tissue anchors 1 and 1'. FIG. 4C illustrates a detailed view of the distal end 80 of introducer needle 81 comprising a recess 82, into which a tissue anchor may be seated.

Figure 5A:
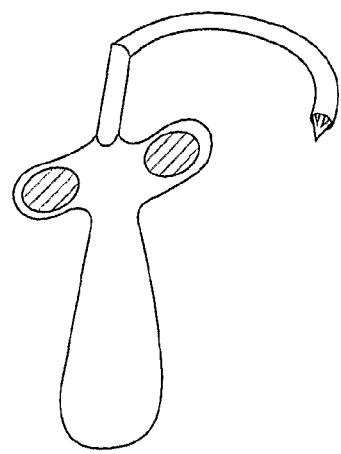
Figure 5B:
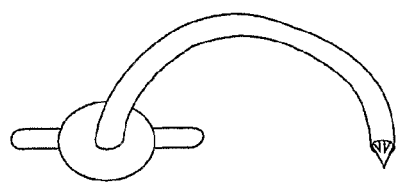
Figure 5C:
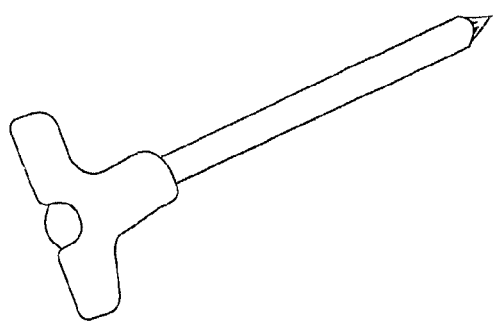

FIGS. 5A-5F illustrate various embodiments of an introducer needle. FIGS. 5A-5B illustrate a side view and top view, respectively, of a halo-shaped introducer shaft typically used for anchoring a support member in the region of the obturator foramina. FIG. 5C illustrates, in accordance with various aspects of the present disclosure, an introducer needle having a straight shaft.

According to various embodiments, the introducer needle can have a small dimensions relative to the introducer needles disclosed in the prior art. For example, the introducer needle can have small curve so that the tissue anchors cannot be inserted too deeply. This can allow for added patient safety during the procedure. The introducer needle can also be designed to have a small handle that can be held in the physician's fingertips or hand to minimize the bulkiness of the introducer and provide optimal tactile control.

Figure 5D:
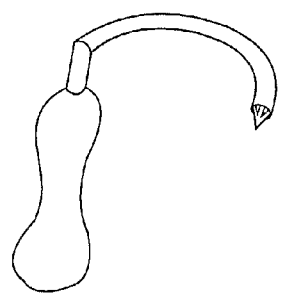
Figure 5E:
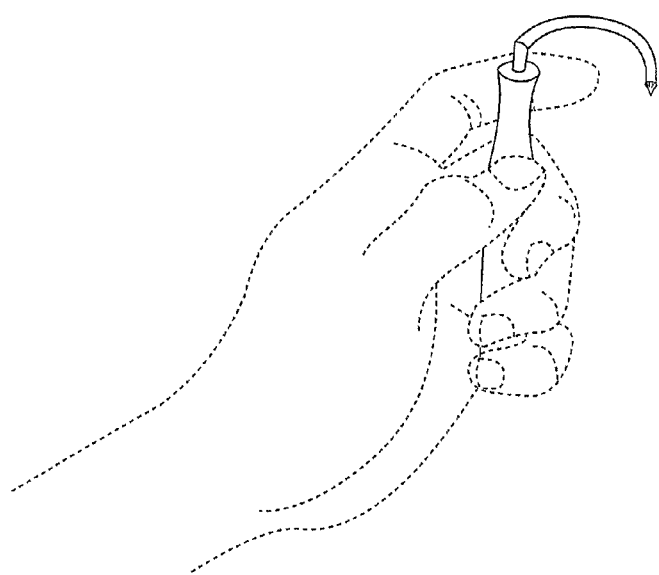
Figure 5F:
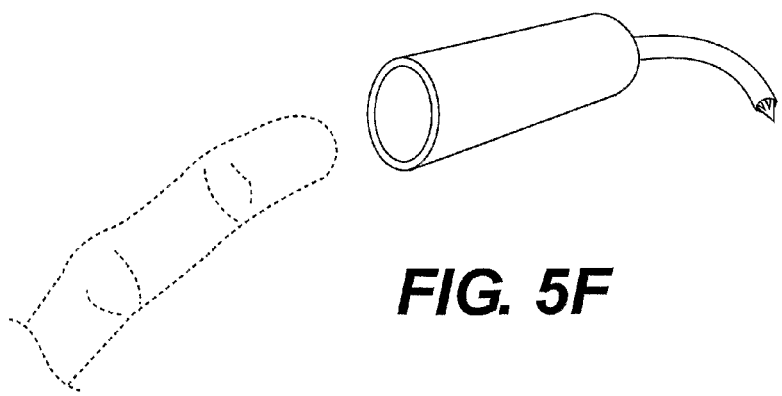

FIGS. 5D-5E illustrate halo introducer needles that are small relative to the needles disclosed in, e.g., U.S. 2006/0015069 (the disclosure of which is incorporated herein by reference in its entirety). In accordance with various embodiments, FIG. 5D illustrates a minimal pivot introducer needle, such that the needle is held by the fingertips as opposed to the entire hand. As shown in FIG. 5E, and in accordance with various embodiments, the index finger can wrap around the back of the needle shaft to urge the distal end (and hence the anchor) into the obturator internus muscle.

Figure 6A:
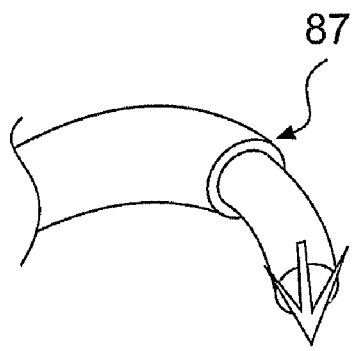
Figure 6B:
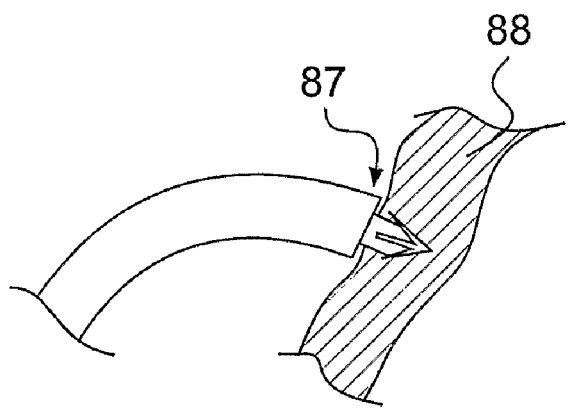

According to various embodiments, it could be desirable to provide an introducer needle with a "stop," or limiting element, that facilitates a limited insertion into the obturator internus muscle. For example, it may be advantageous to insert the tissue anchors into the obturator internus muscle without penetrating the obturator membrane. The needle illustrated in FIGS. 6A and 6B provide an element 87 that permits tactile feel when the distal end of the introducer needle is seated in the internus muscle 88, thereby signaling to the physician that the desired location is reached and further needle progression should stop.

The introducer needle in accordance with various aspects of the present disclosure comprises a distal end with a deployment head that holds the tissue anchor during positioning. When the tissue anchor is positioned in a desired location, the introducer can release the anchor either passively by retracting the introducer, or actively with a push-button, slide, or similar mechanism. The deployment head may also provide a means for compressing the barbs of the anchor so that there is less resistance when inserting the anchor into the tissue. After the anchor is deployed, the barbs can spring outward to lock into the surrounding tissue.

Figure 7:
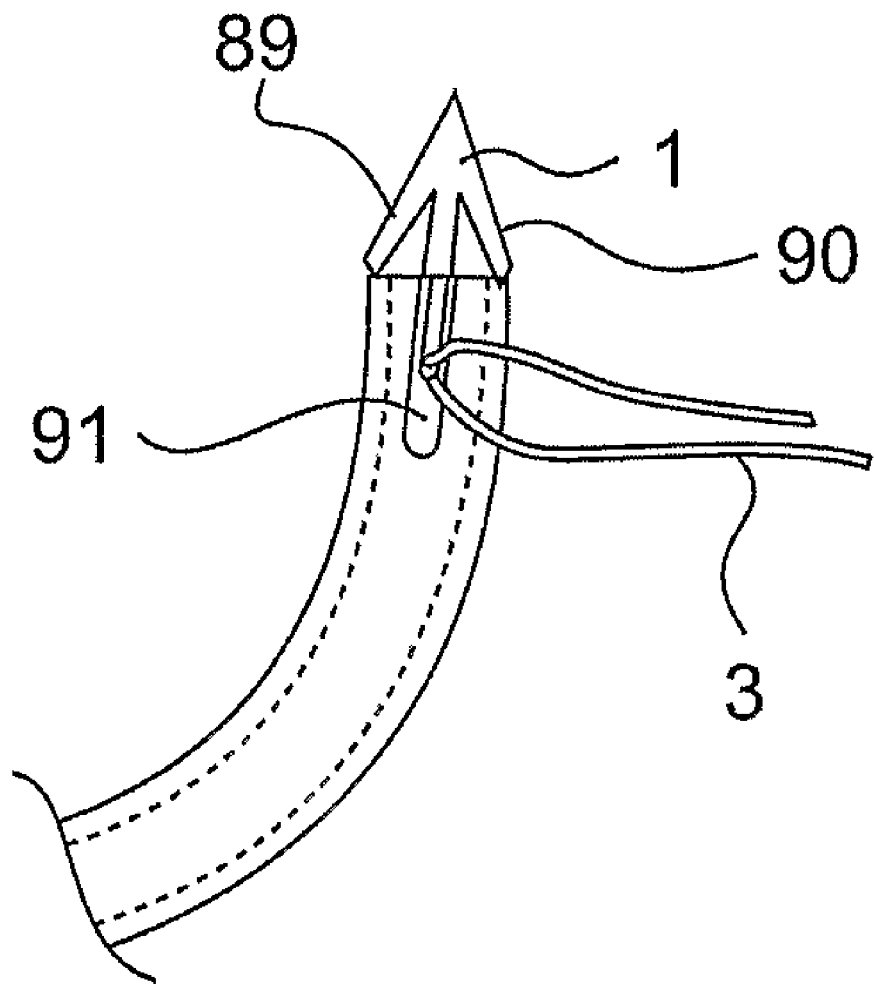
FIG. 7 illustrates one embodiment of an anchor seated in an introducer needle in accordance with various aspects of the present disclosure

Alternatively, and according to various embodiments, the deployment head can shield the barbs on the anchor to prevent the barbs from anchoring into the surrounding tissue until after deployment. As illustrated in FIG. 7, anchor 1 is seated at the distal end of introducer needle 81. The anchor barbs 89 and 90 are substantially flush with the circumference of the needle shaft. According to this aspect of the disclosure, the anchor barbs do not grasp in tissue until the anchor is deployed. The distal end of needle 81 comprises at least one slot 91, through which the filamentary element 3 may extend. According to various embodiments, in order to minimize tissue trauma during needle introduction, the distal end of the needle may be designed so that it is disposed substantially under the distal tip of the anchor.

Figure 8A:
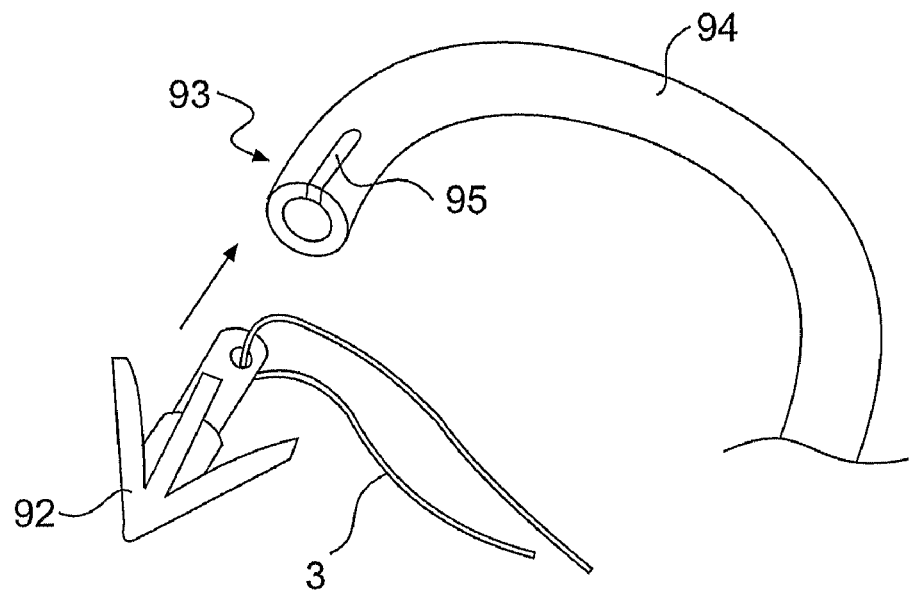
FIGS. 8A-8B illustrate mounting an anchor to an introducer needle, in accordance with various aspects of the present disclosure.
Figure 8B:
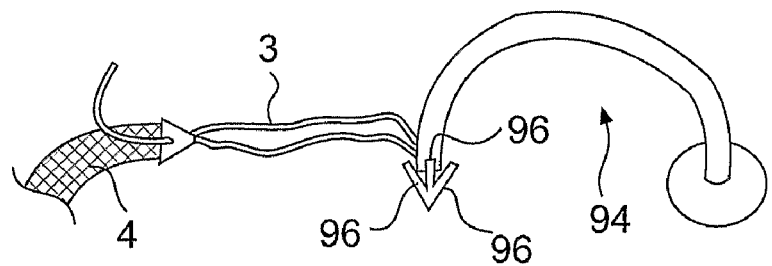
Figure 9:
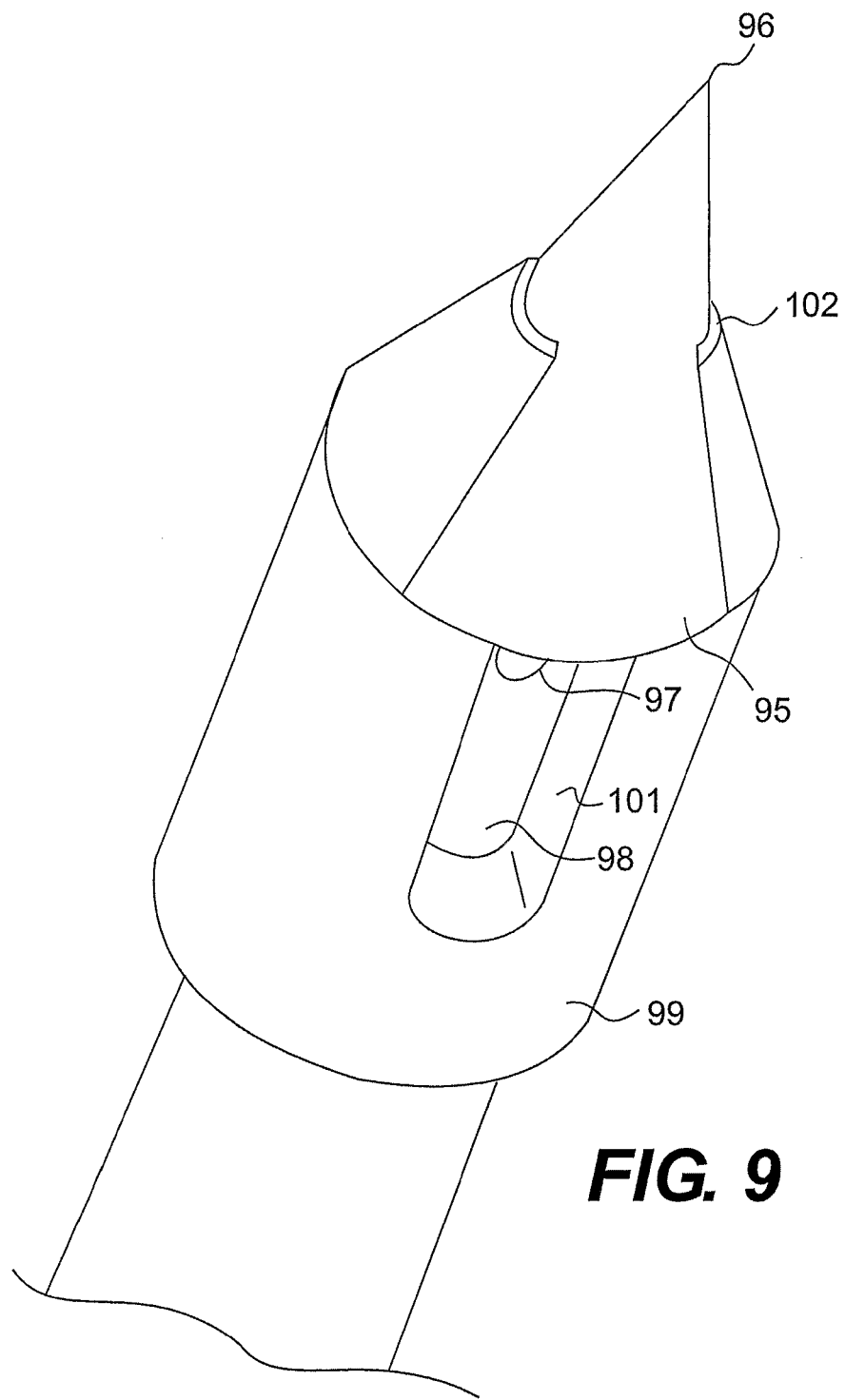
FIG. 9 illustrates another embodiment of an anchor seated in an introducer needle in accordance with various aspects of the present disclosure.

According to another embodiment, and as illustrated in FIGS. 8A and 8B, the anchor barbs may be exposed while the anchor is connected to the distal end of the needle. This configuration is best suited for one-way deployment—that is, the needle may be inserted only in a single direction while connected to the anchor. Anchor 92 can be seated in distal end 93 of introducer needle 94. The distal end comprises a slot 95 for receiving the filamentary element 3. As illustrated in FIG. 11B, which shows an anchor seated in a halo needle, the barbs 96 extend outwardly from the introducer needle 94.

Figure 13:
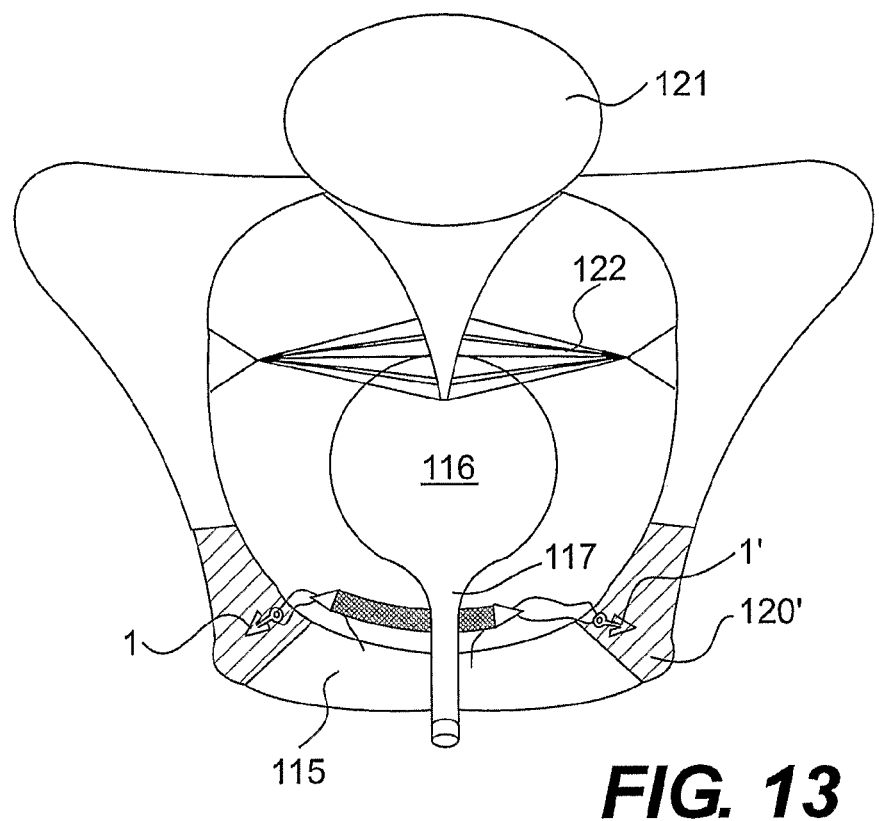
FIG. 13 illustrates an implanted support member, in accordance with various aspects of the present disclosure.

FIG. 13 illustrates a detailed view of an anchor seated in the distal end of a needle. The anchor has a first barb 95, and a second barb (not shown) on the opposite side of the anchor. The anchor has a tip 96 designed to penetrate tissue, an aperture 97 for receiving and holding a filamentary element, and a proximal base portion 98 in which the aperture 97 is disposed. The distal end 99 of the needle comprises at least one slot 101 through which the filamentary element may extend. In order to minimize tissue trauma during insertion of the needle, it can be desirable to have a tight fit between the distal-most end of the needle 102 and the anchor.

Figure 10:
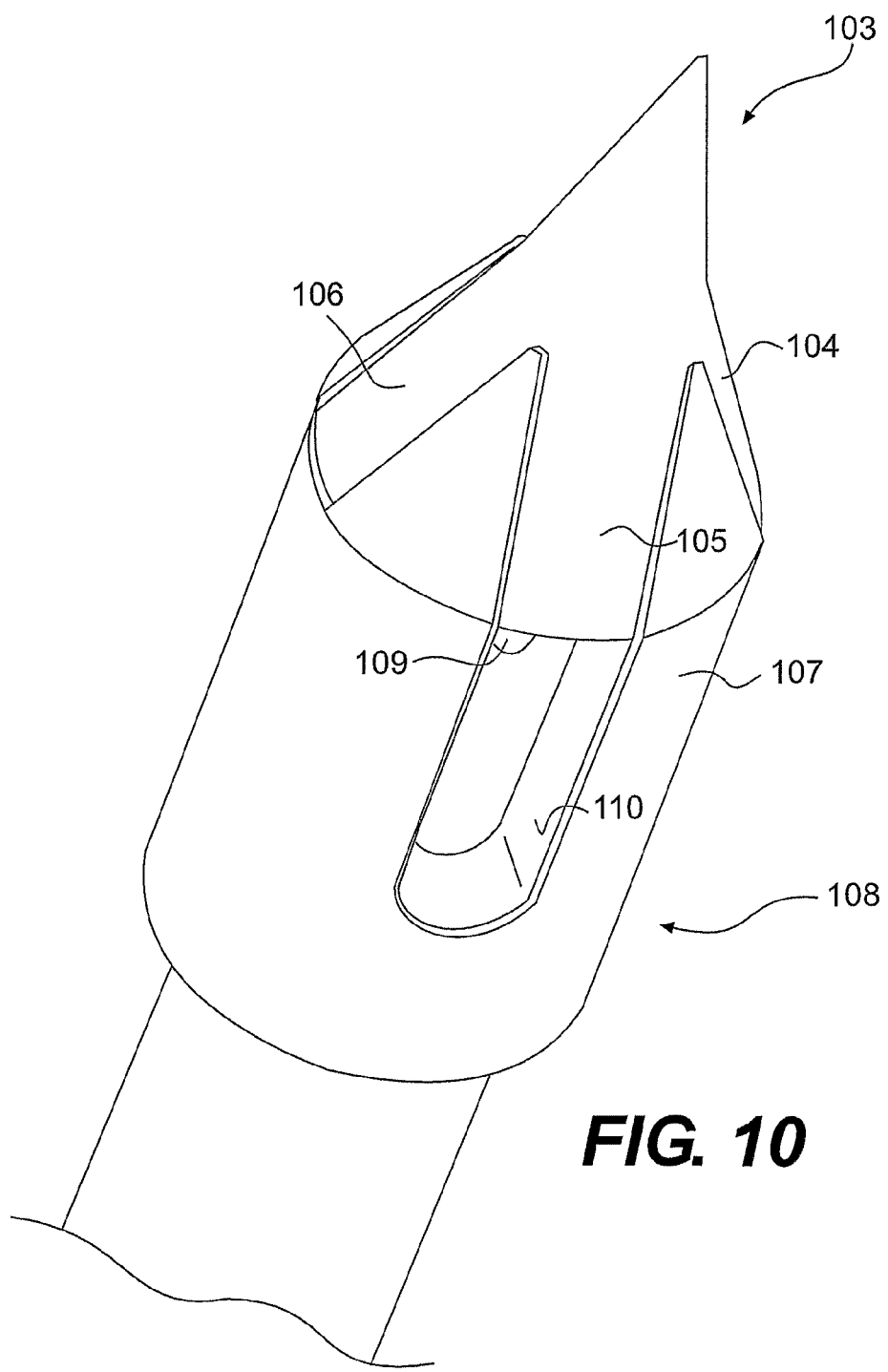
FIG. 10 illustrates another embodiment of an anchor seated introducer needle in accordance with various aspects of the present disclosure.

According to various embodiments, FIG. 10 illustrates a detailed view of an introducer needle having seated therein an anchor 103 with four barbs 104, 105, and 106 (the fourth is not shown). The anchor is designed to fit snugly in the distal end 107 of introducer needle 108. According to various embodiments, anchor 103 contains an aperture 109 through which a filamentary element can be drawn. Distal end of needle 110 contains at least one slot, through which a filamentary element can extend.

Figure 11:
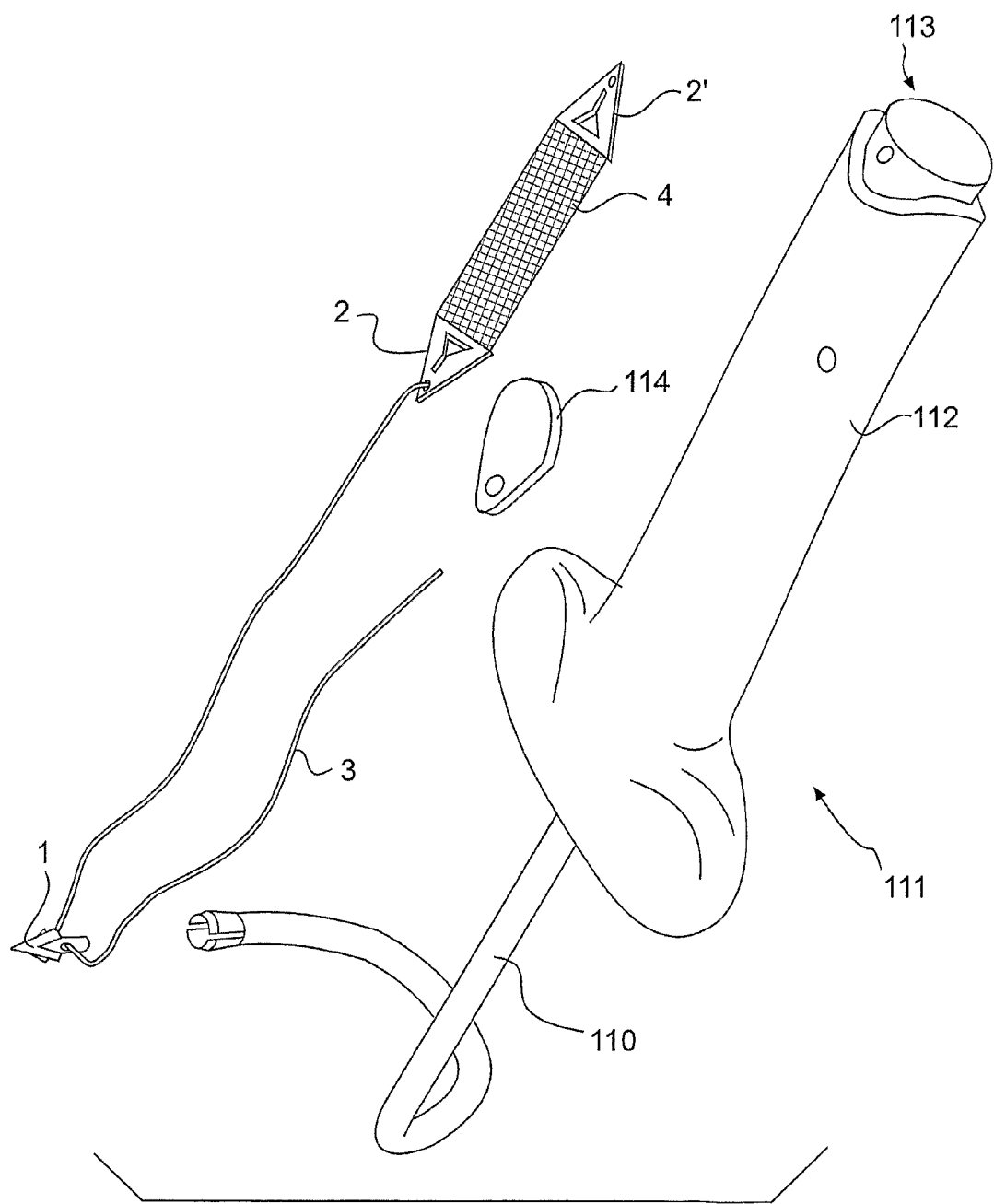
FIG. 11 illustrates one embodiment of certain components of a kit, in accordance with various aspects of the present disclosure.

FIG. 11 illustrates portions of a kit, in accordance with various embodiments, that can be used for implanting a supportive element underneath the urethra. The kit can comprise an introducer needle 111 with a halo-shaped needle shaft 110, a handle 112 and a button 113 for releasing the anchor 1 from the distal end of the needle. Also shown is a filamentary element 3, a support member 4 having two connectors 2 and 2', and a tab 114 that may be secured to the free end of filamentary element 3. According to various embodiments, the kit can further include at least one additional filamentary element and an additional halo needle. According to various embodiments, the needle shaft 110 may be detachable from handle 112, so that a kit may comprise one needle handle 112 and two needle shafts.

According to various embodiments, when the system is used as a sling to support the urethra, an exemplary procedure can comprise at least one of attaching the tissue anchor to an introducer needle, passing the introducer needle through a small vaginal incision beneath the urethra, rotating the introducer needle to insert the anchor into the obturator internus muscle, and releasing the anchor from the introducer needle. The procedure is then repeated on the other side of the urethra so that two anchors are deployed laterally to provide support to the sling. The end of at least one of the filamentary elements is grasped and pulled to position the support member in the desired location, and then secured in the connector via, for example, a cleating element. According to various embodiments, the anchors provide lateral fixation to the sling, while the support member is adjusted independently of the anchor location to provide the desired support. Following the tensioning step, the free ends of the filamentary elements may be trimmed near the connectors to remove excess material. The vaginal incision is then closed, and the procedure is complete.

According to various embodiments, each of the tissue anchors is placed laterally into each obturator internus muscle. The anchors can penetrate into this muscle and fascial lining to provide anchoring outside of, and lateral to, the retropubic space, i.e., the space of Retzius. This region around the obturator membrane has a well-defined anatomical structure, and provides a solid anchoring location for securing tissue anchors. This space is bordered by the inner bony rim of the obturator foramen. According to various aspects of the disclosure, the tissue anchors are not required to pass through the obturator foramina in order to provide sufficient anchoring—only into the obturator internus muscle and/or the obturator membrane.

According to various embodiments, the support members disclosed herein can be inserted via a single vaginal incision. In embodiments where the tissue anchors are secured in the respective obturator internus muscles, the sling arms do not need to exit through skin incisions (which is how the tension exerted by the sling on the urethra is typically adjusted). Instead, the filamentary element is used to adjust the position and tension of the sling.

Figure 12:
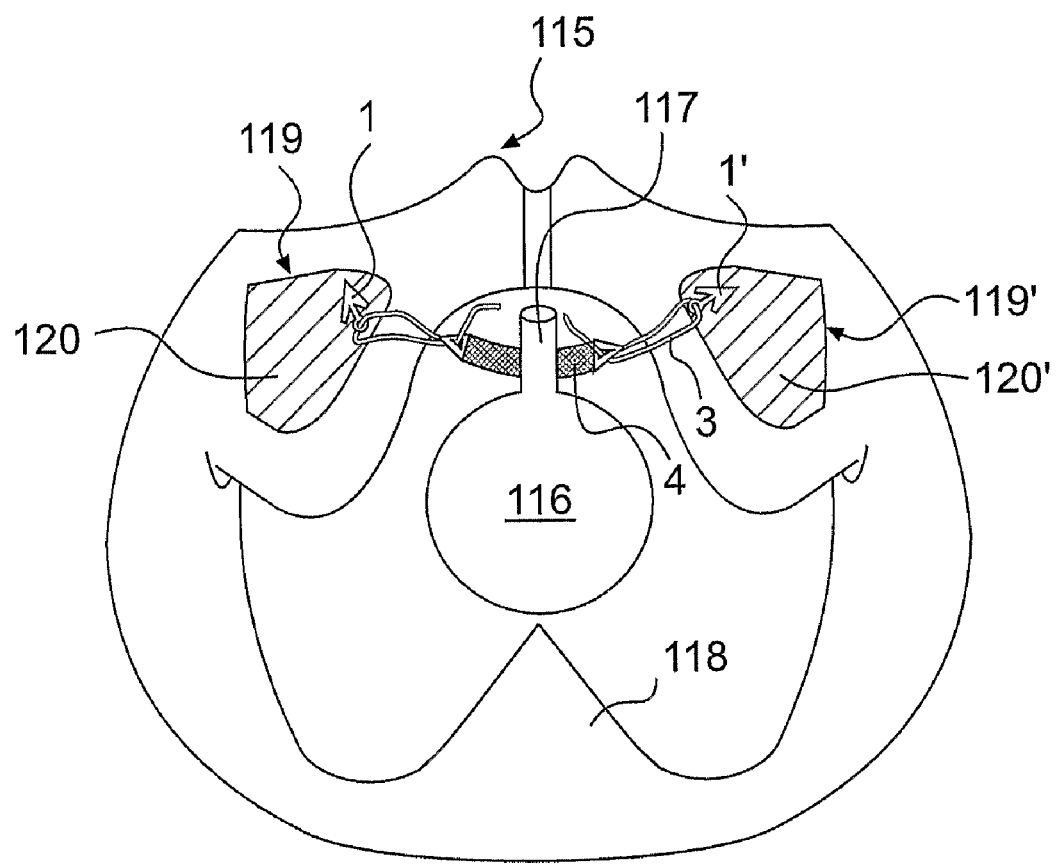
FIG. 12. illustrates a top-down view of a pelvis, with tissue anchors embedded in the obturator internus muscle, in accordance with various aspects of the present disclosure.

FIG. 12 illustrates an exemplary placement of a urethral sling in accordance with various embodiments. With a top-down view of the pelvis from behind, the pubic symphasis 115, bladder 116, urethra 117, sacrum 118, obturator foramina 119 and 119', and obturator internus muscle 120 and 120' can be seen. In accordance with various embodiments, the support member 4 is disposed beneath the urethra 117, and anchors 1 and 1' are secured in the obturator internus muscle.

Figure 14:
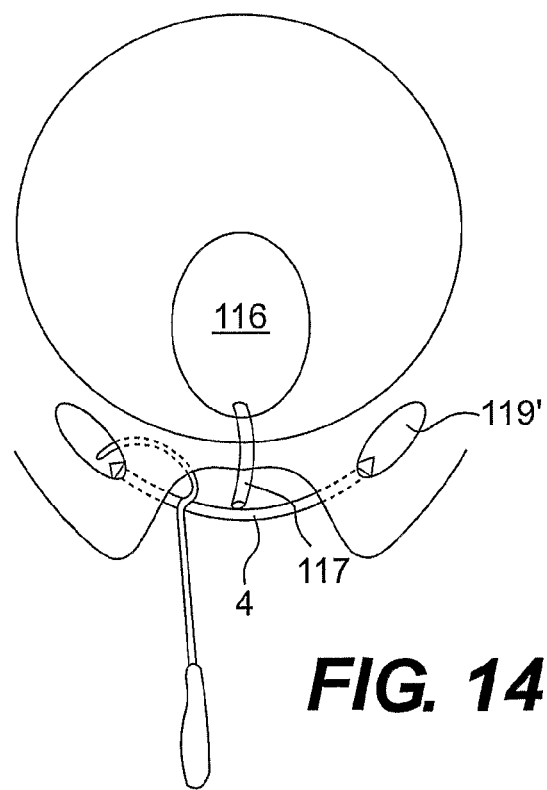
FIG. 14 illustrates an anchor being inserted by an introducer needle, in accordance with various aspects of the present disclosure.

FIG. 13 illustrates a top-down view into the pelvis, including spine 121, and sacrospinous ligament 122. According to various embodiments, anchors 1 and 1' are secured in the obturator internus muscle and optionally into, but not through, the obturator membrane. FIG. 14 illustrates a view showing the placement of anchor 1 into the obturator internus muscle.

Figure 15:
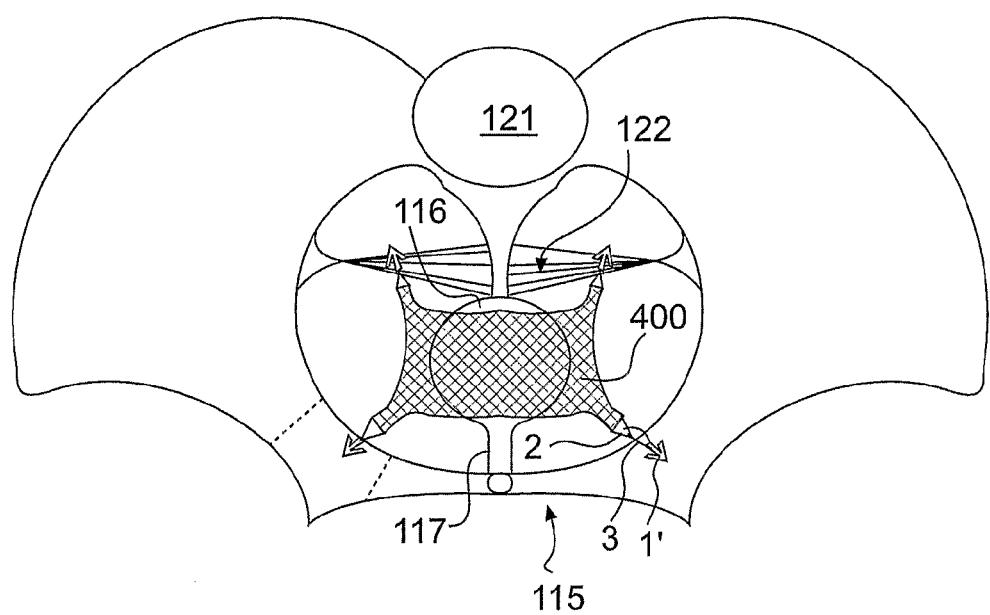
FIG. 15 illustrates a top-down view of a pelvis and an anchored support member supporting the bladder, in accordance with various aspects of the present disclosure.

For applications other than a urethral sling, the support member may have a rectangular or other irregular shape to provide broader support to organs such as the bladder, rectum, bowel, etc. The support member may have multiple arms, with tissue anchors providing multiple points of support around the perimeter of the central support member. The support member may also be positioned at the vaginal apex, with the arms having anchors that are secured to the sacrospinous or uterosacral ligaments to provide apical support to the vaginal vault. According to various embodiments, FIG. 15 illustrates the position of implant 400, which is used for pelvic floor repair.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how several forms of the invention may be embodied in practice.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Also, unless otherwise indicated, all numbers expressing quantities of physical parameters and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Numerical ranges given throughout this specification will include every narrower numerical range that falls within such broader numerical range, as if such narrower numerical ranges were all expressly written herein.

What is claimed is:

1. An implantable system comprising:
   at least two tissue anchors;
   at least two filamentary elements adapted to be associated with the at least two tissue anchors; and
   a support member comprising at least two connectors, a first connector permanently attached to a first filamentary element and a second connector adapted to associate the support member with a second filamentary element, the first connector comprising a first perforation for receiving a second end of the first filamentary element and a fixation feature separate from the first perforation to releasably secure the first filamentary element, the fixation feature comprising a cleating member contiguous with a second perforation,
   wherein at least one of the at least two connectors is adapted to adjustably and releasably fix an end of at least one of the at least two filamentary elements.

2. The implantable system according to claim 1, wherein the support member has a first end, a second end, and a support portion, and wherein each of the first and second ends terminates in one of the at least two connectors.

3. The implantable system according to claim 1, wherein at least one of the at least two anchors includes an aperture to receive an end of at least one of the at least two filamentary elements.

4. The implantable system according to claim 1, wherein said system is configured to treat at least one of a cystocele and a rectocele.

5. The implantable system according to claim 1, wherein the filamentary elements are chosen from mesh, biological material, and suture.

6. The implantable system according to claim 1, wherein the first filamentary element creates a loop from the first connector to at least one of the at least two tissue anchors back to the first connector.

* * * * *